(12) United States Patent
Tian et al.

(10) Patent No.: US 8,884,021 B2
(45) Date of Patent: Nov. 11, 2014

(54) PROCESS FOR PREPARING RACEMIC NICOTINE

(75) Inventors: Guanghui Tian, Shanghai (CN); Guan Wang, Shanghai (CN); Xiaoguang Kong, Shanghai (CN); Rongxia Zhang, Shanghai (CN); Weiming Chen, Shanghai (CN); Jingshan Shen, Shanghai (CN)

(73) Assignees: Topharman Shanghai Co., Ltd., Shanghai (CN); Topharman Shandong Co., Ltd., Shandong (CN)

(*) Notice: Subject to any disclaimer, the term of this patent is extended or adjusted under 35 U.S.C. 154(b) by 0 days.

(21) Appl. No.: 13/982,095

(22) PCT Filed: Jan. 20, 2012

(86) PCT No.: PCT/CN2012/070630
§ 371 (c)(1),
(2), (4) Date: Oct. 15, 2013

(87) PCT Pub. No.: WO2012/100722
PCT Pub. Date: Aug. 2, 2012

(65) Prior Publication Data
US 2014/0031554 A1 Jan. 30, 2014

(30) Foreign Application Priority Data
Jan. 27, 2011 (CN) .......................... 2011 1 0029313

(51) Int. Cl.
*C07D 401/04* (2006.01)
*C07D 401/06* (2006.01)

(52) U.S. Cl.
CPC ............ *C07D 401/04* (2013.01); *C07D 401/06* (2013.01)
USPC ...................................... 546/279.4

(58) Field of Classification Search
CPC ...................................... C07D 401/04
USPC ...................................... 546/279.4
See application file for complete search history.

(56) References Cited

PUBLICATIONS

International Preliminary Report on Patentability issued in International Patent Application No. PCT/CN2012/070630 dated Apr. 19, 2012 (with translation).
P. Gartner et al., "Synthesis of Partially Deuterated N-Nitrosamines-New Standards in Tobacco-smoke Analysis", Monatsherte Fur Chemie, 2004, col. 135, No. 5, pp. 549-555.
D. Dhimant et al., "Synthesis of Isotope-labeled Tobacco-Specific Nitrosamines and their Metabolites", Journal of Labelled Compounds and Radiopharmaceuticals, 2008, vol. 51, No. 5, pp. 226-230.
P. Tanmaya et al., Synthesis of [4-2H2]-, (4R)[4-2H1)- and (4S)[4-2H1]-41(methylnitrosamino)-1-(3'pyridy1)-1-butanone, C-4 Deuteriated isotopomers of the procarcinogne NNK, Tetrahedron, 1990, vol. 6, No. 5, pp. 1733-1744.
International Search Report for PCT/CN2012/070630 mailed Apr. 19, 2012.
P. Tanmaya et al., Synthesis of [4-2H2]-, (4R)[4-2H1)- and (4S)[4-2H1]-41(methylnitrosamino)-1-(3'pyridyl)-1-butanone, C-4 Deuteriated isotopomers of the procarcinogne NNK, Tetrahedron, 1990, vol. 6, No. 5, pp. 1733-1744.

*Primary Examiner* — Patricia L Morris
(74) *Attorney, Agent, or Firm* — Nixon & Vanderhye, P.C.

(57) ABSTRACT

Provided is a process for preparing racemic nicotine from 1-methyl-3-nicotinoyl-2-pyrrolidone or a salt thereof using one-pot process. The process comprises the following steps: 1) in a reaction vessel, reacting 1-methyl-3-nicotinoyl-2-pyrrolidone or a salt thereof in the presence of a suitable solvent and a strong acid by heat; after the reaction is complete, cooling the same and adjusting the pH to 7-8 with alkali; and 2) directly adding a reductant into the above vessel, and after the reaction, purifying the product so as to obtain high purity racemic nicotine or a salt thereof.

13 Claims, No Drawings

PROCESS FOR PREPARING RACEMIC NICOTINE

This application is the U.S. national phase of International Application No. PCT/CN2012/070630 filed 20 Jan. 2012 which designated the U.S. and claims priority to CN 201110029313.6 filed 27 Jan. 2011, the entire contents of each of which are hereby incorporated by reference.

TECHNICAL FIELD

The present invention relates to a process for preparing racemic nicotine (I), in particularly, to a process for preparing racemic nicotine or a salt thereof from 1-methyl-3-nicotinoyl-2-pyrrolidone or a salt thereof using one-pot process.

BACKGROUND

In 1990s, nicotine replacement therapy is widely promoted in the world by World Health Organization to help the people to overcome the dependency on cigarette in physiology and mental, so as to give up smoking. It has been proved in clinic that nicotine is a promising and efficient drug for treating Alzheimer's disease, Parkinson's syndrome and depression. Racemic nicotine has an essentially similar pharmacological effect to natural (levogyric) nicotine, except that it is a little poor in the potential and action period relative to levogyric nicotine, but it has a much lower toxicity than that of levogyric nicotine.

Currently, the commercially available levogyric nicotine is mainly from the extract of plant, thus its use is influenced by various factors such as raw material, climate, period, etc. but racetic nicotine can be obtained only by synthesizing.

It is reported in Journal of Organic Chemistry, 1990, 55(6), 1736-44 that racemic nicotine may be synthesized from pyrrolidine by a four-step reaction, which is shown in the following reaction scheme 1.

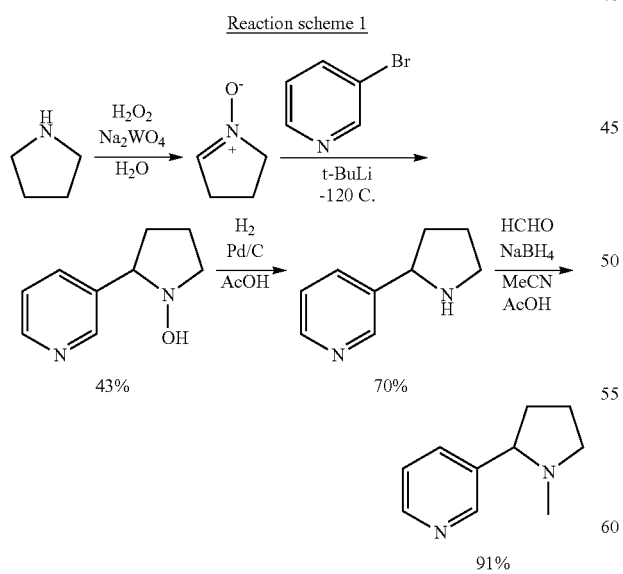

Reaction scheme 1

The tert-butyl lithium and the low temperature of −120° C. in the reaction involved in this document increase the difficulty of industrial production and this method has a lower yield.

Another method reported in Journal of the Chemical Society, Perkin Transactions I, 2002(2), 143-154 prepares racemic nicotine from nicotinic acid by a four-step reaction, which is shown in the following reaction scheme 2.

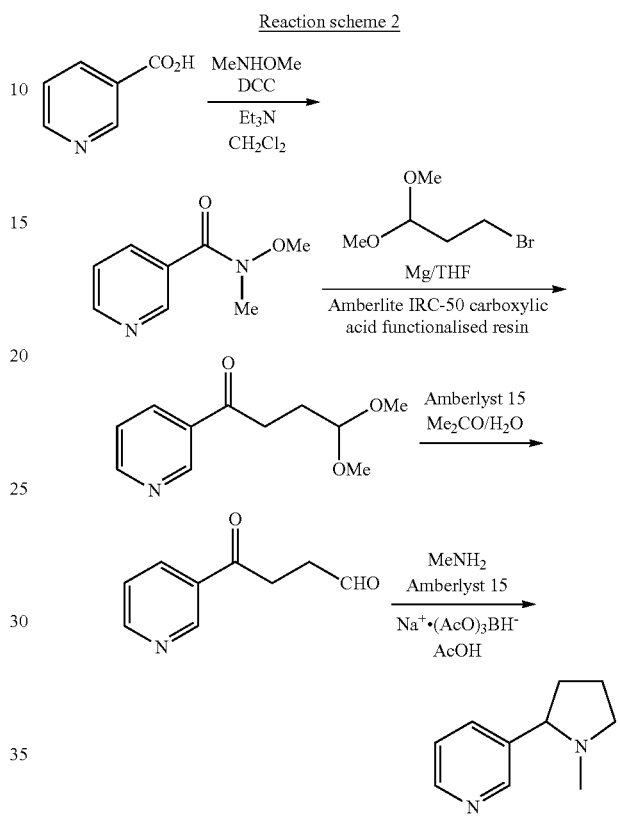

Reaction scheme 2

Grignard reagent used in this document also restricts the use of the method in industry.

Later, it was reported in Synlett, 2009(15), 2497-2499 that racemic nicotine may be prepared from 3-pyridylaldehyde as a raw material, which is shown in the following reaction scheme 3.

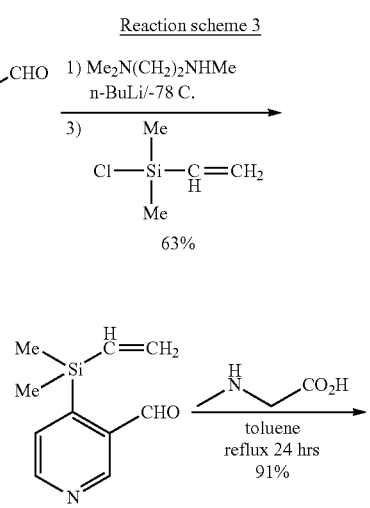

Reaction scheme 3

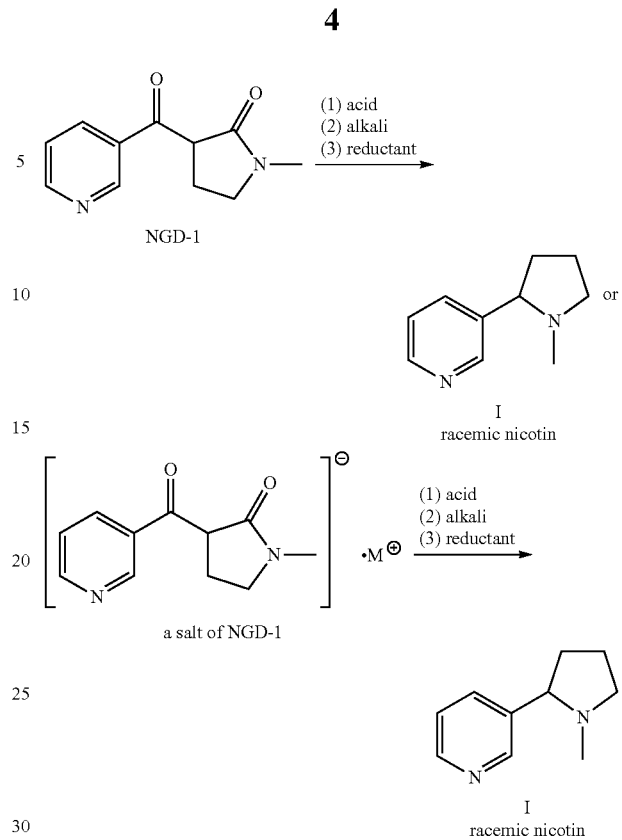

NGD-1 racemic nicotin a salt of NGD-1 racemic nicotin

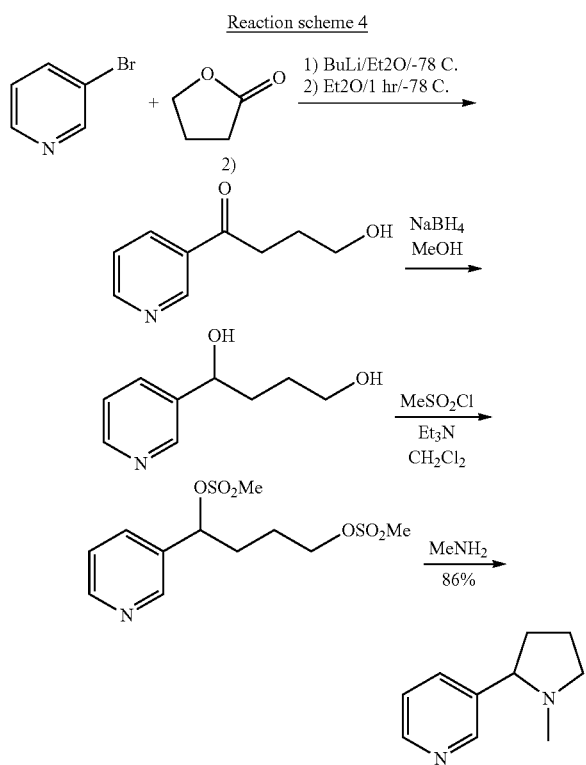

Similarly as above, this method still can not substantially eliminate the problem that racemic nicotine is difficult to be produced in industry.

A method for preparing racemic nicotine reported in Journal of Heterocyclic Chemistry, 2009, 46(6), 1252-1258, is shown in the following reaction scheme 4.

Reaction scheme 4

It is also impossible to produce racemic nicotine in large scale, since butyl lithium is used to perform a metal exchange reaction with 3-bromopyridine at low temperature.

In sum, the current methods for preparing racemic nicotine are difficult to be used in industry production, since they not only use expensive reagents, but also are generally performed at low temperature with multiple steps and longer reaction period, and the separation and purification in each step are complicated, increasing the production cost.

SUMMARY OF THE INVENTION

Aiming at the defects in the art, the object of present invention is to provide a process for preparing racemic nicotine by one-pot synthesis, which is represented by the following scheme:

wherein, M is potassium (K), sodium (Na) or lithium (Li).

The present process can be performed easily and in a low cost, and is suitable for industrial production. The "one pot process" is a process in which a plural of reactions are carried out in one reactor without separating and purifying the intermediate, while only the final reaction solution is dealt by separating and purifying.

To achieve the above object, the present invention provides a process for preparing racemic nicotine, comprising the following steps of:

1) reacting 1-methyl-3-nicotinoyl-2-pyrrolidone (NGD-1) or a salt thereof in the presence of a suitable solvent and a suitable strong acid under heat in a reactor, and then cooling the reaction mixture after the reaction is completed and adjusting to pH 7-8 with a base;

2) directly adding a reductant into the above reactor, and then purifying the product after the reaction is completed to obtain racemic nicotine.

In one embodiment of present invention, in step 1), the salt of NGD-1 is potassium salt, sodium salt or lithium salt.

In one embodiment of present invention, in step 1), the suitable solvent is selected from water, methanol, ethanol, iso-propanol, tert-butanol, ethylene glycol and ethylene glycol monomethyl ether, or a mixture thereof.

In another embodiment of present invention, in step 1), the suitable strong acid is selected from hydrochloric acid, sulfuric acid, phosphoric acid, nitric acid, hydrobromic acid, hydriodic acid, perchloric acid, trifluoromethanesulfonic acid, trifluoracetic acid, trichloroacetic acid, citric acid, tartaric acid and maleic acid, or a mixture thereof in any ratio.

The reaction temperature in the presence of acid may be from 50 to 300° C.; and the strong acid may be used in an amount of 0.1-100 times (molar ratio) of that of NGD-1 or a salt of NGD-1.

In a still another embodiment of present invention, in step 1), the base for adjusting pH value is selected from alkali metal alkoxides such as sodium methoxide, sodium ethoxide and potassium tert-butoxide; alkali metal oxides; amines such as triethylamine and diisopropylethylamine; metal salts of amine such as NaHMDS and LDA; hydroxides such as sodium hydroxide, lithium hydroxide and magnesium hydroxide; carbonates such as sodium carbonate, potassium carbonate and cesium carbonate; and bicarbonates such as sodium bicarbonate; or a mixture thereof in any ratio. It is preferred to use the base selected from sodium hydroxide, potassium hydroxide, lithium hydroxide, cesium hydroxide, calcium hydroxide, magnesium hydroxide and a mixture thereof in any ratio.

In still another embodiment of present invention, in step 2), the reductant is a general reductant in organic chemistry, which comprises metal borohydrides such as sodium borohydride, potassium borohydride and sodium cyanoborohydride; borane; hydrogen (optionally, the reduction is one catalyzed by nickel, palladium, platinum, rhodium, ruthenium, etc., such as activity nickel and hydrogen, palladium on carbon and formic acid); reduction catalyzed by a compound containing a metal element selected from nickel, palladium, platinum, rhodium and ruthenium (for example, reduction catalyzed by ruthenium hydrochloride and triphenylphosphine complex); iron; zinc; a reductant containing iron, zinc, tin and aluminum element, such as tin dichloride. As a preferable solution, sodium borohydride, potassium borohydride, tetrahydro-lithium aluminum, iron powder, zinc powder and tin dichloride are preferred.

In still another embodiment of present invention, in step 2), the purification is performed by stream distillation or extraction by using a general solvent such as petroleum ether, dichloromethane, ethyl acetate, chloroform, etc.

In present invention, the reductant may be added into the reactor directly. After the reaction is completed, the reaction solution is distilled directly to obtain an aqueous nicotine solution with a purity of 98% or more, which is then concentrated under reduced pressure to give a racemic nicotine with high purity. In addition, an organic solvent may used to extract the nicotine, the racemic nicotine with high purity may be obtained after the solvent is concentrated under reduced pressure. The example of the organic solvent may be one selected from petroleum ether, dichloromethane, ethyl acetate or chloroform.

Another method is salification purification, which is a purification method by dissolving nicotine in a solvent, adding an organic or inorganic acid, and precipitating to give a salt.

The solvent for dissolving the nitotine may be selected from water, methanol, ethanol, ethyl acetate, dichloromethane, chloroform, toluene, tetrahydrofuran, petroleum ether and n-hexane, or a mixture thereof in any ratio.

The organic acid is preferably formic acid, acetic acid, maleic acid, citric acid, fumaric acid, p-toluenesulfonic acid, picric acid, malic acid or glycine.

The inorganic acid is preferably hydrochloric acid, sulfuric acid, phosphoric acid, oxalic acid or methanesulfonic acid.

The present invention also provides a salt of NGD-1 and a process for preparing the same.

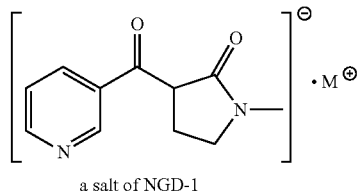

a salt of NGD-1 wherein, M is potassium (K), sodium (Na) or lithium (Li).

The salt of NGD-1 may be prepared by dissolving N-methylpyrrolidone and a nicotinate in an organic solvent such as toluene in the presence of a strong base. NGD-1 may be obtained from the salt thereof by adjusting the pH value to be acidic.

The nicotinate is preferably methyl nicotinate, ethyl nicotinate or tert-butyl nicotinate. The strong base is sodium hydroxide, potassium hydroxide, sodium hydride, sodium tert-butoxide, potassium tert-butoxide or lithium tert-butoxide.

According to the present process for preparing racemic nitotine, four reaction steps comprising ring-opening, decarboxylation, cyclization and reduction are combined and performed in one reactor without requiring separating and purifying the intermediate, while only the final reaction solution needs to be dealt by separating and purifying, thus the present process reduces the product loss in the operation steps, simplifies the process procedures and decreases the production cost. Moreover, the present process for preparing nicotine has the advantages in that the raw material is cheap, the reaction does not need low temperature and the operation is simple, showing that the present process is a simple and economic process suitable for industrial production.

BEST MODE

The following examples are only for illustrating the preferred embodiments of the present invention and should not be construed to restrict the technical solution of present invention. Any simple modification to the present preparing process under the concept of the present invention will fall into the protection scope of the present invention.

The solvent or reagent used in the examples was purchased from Chemical reagent Ltd. of National Pharmaceutical Group. The melting point was measured on a BUCHI-510 meldometer and the temperature is not calibrated. Mass spectra were recorded on a Finnigan MAT-95 mass spectrometer. $^1$H NMR was completed in a Varian Mercury 300 apparatus and each spectrum is consistent with the predicted structure, in which the following general abbreviations are used to represent the characteristic peak: s: unimodal; d: bimodal; t: triplet; q: quartet; m: multiplet. The room temperature means 20-25° C.

Example 1

The Preparation of Racemic Nicotine 1-methyl-3-nicotinoyl-2-pyrrolidone (11.3 g, 0.055 mol) was dissolved in a 6N hydrochloric acid (125 mL) The solution was heated at 135° C. in an oil bath for 40 h and then cooled to room temperature. The pH of the mixture was adjusted to 8 by using 4 mol/L sodium hydroxideunder an ice-water bath, and then sodium borohydride (2.4 g) was added therein under ice-water bath. The mixture was stirred for 1.5 h after the ice-water bath was removed. The reaction solution was extracted with dichloromethane, dried and concentrated to obtain a crude product as a yellowish oil. 100 mL water was added and the mixture was stream-distilled directly. After the water was extracted with petroleum ether, the extract was dried and concentrated to obtain an oily product (7.8 g, yield 71%). HPLC purity 98.2%. $^1$H NMR (CDCl$_3$, 300 MHz) δ: 8.52 (d, 1H), 8.48 (dd, 1H), 7.69 (dt, 1H), 7.25 (dd, 1H), 3.23 (t, 1H), 3.07 (t, 1H), 2.29 (m, 1H), 2.16 (s, 3H), 1.90-2.04 (m, 2H), 1.65-1.88 (m, 2H); ESI-MS 163.4 (M+H).

Example 2

The Preparation of Racemic Nicotine 1-methyl-3-nicotinoyl-2-pyrrolidone (20.4 g, 0.1 mol) was dissolved in a 6N hydrochloric acid (150 mL) The solution was heated to 135° C. to react for 8 h and then cooled to room temperature. The pH of the mixture was adjusted to 7 by using NaOH under an ice bath, and then potassium borohydride (5.3 g, 0.1 mol) was added therein and the temperature was back to room temperature for 2 h. 200 mL distilled water was added and the mixture was stream-distilled. The distilled water phase was concentrated till dry to give 12.2 g racemic nicotine. HPLC purity 98.4%; $^1$H NMR (CDCl$_3$, 300 MHz) δ: 8.52 (d, 1H), 8.48 (dd, 1H), 7.69 (dt, 1H), 7.25 (dd, 1H), 3.23 (t, 1H), 3.07 (t, 1H), 2.29 (m, 1H), 2.16 (s, 3H), 1.90-2.04 (m, 2H), 1.65-1.88 (m, 2H), ESI-MS 163.4 (M+H).

Example 3

The Preparation of Racemic Nicotine 1-methyl-3-nicotinoyl-2-pyrrolidone (20.4 g, 0.1 mol) was dissolved in a 6N hydrochloric acid (150 mL) The solution was heated to 100° C. to react for 24 h and then cooled to room temperature. The pH of the solution was adjusted to 7 by using KOH under an ice bath, and then potassium borohydride (5.3 g, 0.1 mol) was added therein and the temperature was back to room temperature for 2 h. 200 mL Distilled water was added and the mixture was then stream-distilled. The distilled water phase was extracted with 300 mL petroleum ether, and the resultant petroleum ether was concentrated till dry to give a colorless oily product (11.0 g). HPLC purity 99.2%; $^1$H NMR (CDCl$_3$, 300 MHz) δ: 8.52 (d, 1H), 8.48 (dd, 1H), 7.69 (dt, 1H), 7.25 (dd, 1H), 3.23 (t, 1H), 3.07 (t, 1H), 2.29 (m, 1H), 2.16 (s, 3H), 1.90-2.04 (m, 2H), 1.65-1.88 (m, 2H), ESI-MS 163.4 (M+H).

Example 4

The Preparation of Racemic Nicotine 1-methyl-3-nicotinoyl-2-pyrrolidone (50.0 g, 0.21 mol) was dissolved in a concentrated hydrochloric acid (150 mL), and the solution was heated to 120° C. to react for 8 h. Then the pH of the solution was adjusted to 8 by using 6 mol/L sodium hydroxide under an ice bath, and then sodium borohydride (4.7 g, 0.12 mol) was added therein under ice bath and the mixture was stirred for 1.5 h at room temperature. The reaction solution was extracted with dichloromethane and the extract was concentrated till dry to obtain a crude product (34 g). ESI-MS 163.4 (M+H).

The crude product was dissolved in absolute ethyl alcohol (100 mL) and oxalic acid monohydrate (23.1 g, 0.21 mol) was added therein. The mixture was heated to 50° C. with stirring to precipitate a white solid. Sucking filtration and drying were performed to obtain 47 g nicotine bisoxalate with HPLC purity of 98.6%.

Example 5

1-methyl-3-nicotinoyl-2-pyrrolidone (47.5 g, 0.21 mol) was dissolved in a concentrated hydrochloric acid (150 mL), and the solution was heated to 140° C. to react for 6 h. Then the pH of the solution was adjusted to 8 by using 6 mol/L sodium hydroxide under an ice bath, and then potassium borohydride (6.5 g, 0.12 mol) was added therein under ice bath and the mixture was stirred for 1 h at room temperature. The reaction solution was extracted with dichloromethane and the extract was concentrated till dry to obtain a crude product (30 g). ESI-MS 163.4 (M+H).

The crude product was dissolved in absolute ethyl alcohol (100 mL) and acetic acid (23.1 g, 0.21 mol) was added therein. The mixture was heated to 50° C. with stirring and concentrated to 50 mL, and then 30 mL ethyl acetate was added to precipitate a white solid. Sucking filtration and drying were performed to obtain 34 g nicotine acetate with a HPLC purity of 98.5%.

Example 6

The Preparation of 1-methyl-3-nicotinoyl-2-pyrrolidone (NGD-1)

Nicotinic acid (10 g, 81.2 mmol) was suspended in absolute ethyl alcohol (80 mL), and concentrated sulfuric acid (10 mL) was added gradually, and then the mixture was heated at 85° C. for 4 h under an oil bath and then distilled under reduced pressure to remove part of ethyl alcohol. Under ice-water bath, the pH of the mixture was adjusted to 7-8 by using concentrated sodium hydroxide aqueous solution. 400 mL ethyl acetate was used to extract the product, and the ethyl acetate phase was washed with sodium bicarbonate, dried over anhydrous sodium sulfate and concentrated till dry to give 10.3 g oily product (ethyl nicotinate), which was directly used in next step without purification.

Ethyl nicotinate (10.3 g, 66 mmol) and N-methyl-2-pyrrolidone (6.5 mL, 66 mmol) were dissolved in a dry toluene (200 mL) and sodium hydride (4 g) was added therein in batch. The mixture was stirred for 30 h under reflux, and then cooled to room temperature, and 5 mL methanol was added to quench the reaction. The reaction solution was poured into 1 mol/L of diluted hydrochloric acid (70 mL), extracted with dichloromethane. The extract was washed with saline and concentrated till dry to give 11.3 g colorless oily product (1-methyl-3-nicotinoyl-2-pyrrolidone) with a yield of 81%. $^1$HNMR (CD$_3$OD, 300 MHz) δ: 9.21 (d, 1H), 8.75 (dd, 1H), 8.48 (dt, 1H), 7.60 (dd, 1H), 4.70 (d, 1H), 3.48-3.57 (m, 1H), 3.41-3.46 (m, 1H), 2.85 (s, 3H), 2.52-2.60 (m, 1H), 2.30-2.38 (m, 1H); ESI-MS 205.0 (M+H), 243.1 (M+K).

Example 7

The Preparation of 1-methyl-3-nicotinoyl-2-pyrrolidone Potassium Salt

Ethyl nicotinate (50.0 g, 0.33 mol) and N-methyl-2-pyrrolidone (32.5 mL, 0.34 mmol) were dissolved in toluene (600 mL) and potassium tert-butoxide (44.5 g, 0.40 mol) was added therein. The mixture was reacted for 3 h under reflux, and suck filtrated to precipitate a solid, which was dried in vacuum to obtain 76.1 g yellowish solid. ESI-MS 205.0 (M+H), 227.0 (M+Na), elemental analysis: C, 54.32; H, 4.38; N, 11.66

Example 8

The Preparation of 1-methyl-3-nicotinoyl-2-pyrrolidone Sodium Salt

Ethyl nicotinate (50.0 g, 0.33 mol) and N-methyl-2-pyrrolidone (32.5 mL, 0.34 mmol) were dissolved in toluene (600 mL) and sodium tert-butoxide (38.1 g, 0.40 mol) was added therein. The mixture was reacted for 4 h under reflux, and suck filtrated to precipitate a solid, which was dried in vacuum to obtain 65.8 g yellowish solid. ESI-MS 205.0 (M+H), 227.0 (M+Na), elemental analysis: C, 58.26; H, 4.68; N, 12.66

Example 9

The Preparation of
1-methyl-3-nicotinoyl-2-pyrrolidone Lithium Salt

Ethyl nicotinate (10.3 g, 66 mmol) and N-methyl-2-pyrrolidone (6.5 mL, 66 mmol) were dissolved in chlorobenzene (100 mL) and lithium tert-butoxide (6.54 g, 82 mmol) was added therein. The mixture was reacted for 6 h under reflux, and suck filtrated to precipitate a solid, which was dried in vacuum to obtain 12.6 g yellowish solid. ESI-MS 205.0 (M+H), 227.0 (M+Na).

The embodiments of present invention have been disclosed above, but it is apparent for a person skilled in the art to vary or modify the present invention without departing from the spirit and scope of present invention defined in the claims.

The invention claimed is:

1. A process for preparing racemic nicotine or a salt thereof by one-pot process, comprising the following steps:
   1) reacting 1-methyl-3-nicotinoyl-2-pyrrolidone or a salt thereof in the presence of a solvent and a strong acid under heat in a reactor, and then cooling the reaction mixture after the reaction is completed and adjusting to pH=7-8 with a base;
   2) directly adding a reductant into the above reactor, and after the reaction is completed, purifying the product to obtain the racemic nicotine or a salt thereof.

2. The process for preparing racemic nicotine or a salt thereof by one-pot process according to claim 1, characterized in that, the salt of 1-methyl-3-nicotinoyl-2-pyrrolidone is potassium salt, sodium salt or lithium salt.

3. The process for preparing racemic nicotine or a salt thereof by one-pot process according to claim 1, characterized in that, in step 1), the solvent is selected from water, methanol, ethanol, iso-propanol, tert-butanol, ethylene glycol and ethylene glycol monomethyl ether, or a mixture thereof.

4. The process for preparing racemic nicotine or a salt thereof by one-pot process according to claim 1, characterized in that, in step 1), the strong acid is selected from hydrochloric acid, sulfuric acid, phosphoric acid, nitric acid, hydrobromic acid, hydriodic acid, perchloric acid and trifluoromethanesulfonic acid.

5. The process for preparing racemic nicotine or a salt thereof by one-pot process according to claim 1, characterized in that, the reaction temperature under heat is from 50 to 300° C.; and in molar ratio, the strong acid is used in an amount of 0.1-100 times of that of 1-methyl-3-nicotinoyl-2-pyrrolidone or a salt of 1-methyl-3-nicotinoyl-2-pyrrolidone.

6. The process for preparing racemic nicotine or a salt thereof by one-pot process according to claim 1, characterized in that, in step 1), the base is selected from alkali metal alkoxide, alkali metal oxide, amine, metal salt of amine, hydroxide, carbonate and bicarbonate, or a mixture thereof in any ratio.

7. The process for preparing racemic nicotine or a salt thereof by one-pot process according to claim 6, characterized in that, the base is selected from sodium hydroxide, potassium hydroxide, lithium hydroxide, cesium hydroxide, calcium hydroxide and magnesium hydroxide, or a mixture thereof in any ratio.

8. The process for preparing racemic nicotine or a salt thereof by one-pot process according to claim 1, characterized in that, the reductant is selected from metal borohydride; borane; hydrogen; iron; zinc; a reductant containing an element selected from iron, zinc, tin, and aluminum.

9. The process for preparing racemic nicotine or a salt thereof by one-pot process according to claim 8, characterized in that, the reductant is sodium borohydride, potassium borohydride, tetrahydro-lithium aluminum or tin dichloride.

10. The process for preparing racemic nicotine or a salt thereof by one-pot process according to claim 1, characterized in that, in step 2), the purification is performed by stream distillation or by salification precipitation of nicotine.

11. The process for preparing racemic nicotine or a salt thereof through a one pot process according to claim 10, characterized in that, the salification precipitation of nicotine is performed by dissolving nicotine in a solvent, adding an organic or inorganic acid, and precipitating to obtain a salt of nicotine.

12. The process for preparing racemic nicotine or a salt thereof by one-pot process according to claim 11, characterized in that, the solvent is selected from water, methanol, ethanol, ethyl acetate, dichloromethane, chloroform, toluene, tetrahydrofuran, petroleum ether and n-hexane, or a mixture thereof in any ratio.

13. The process for preparing racemic nicotine or a salt thereof by one-pot process according to claim 11, characterized in that, the organic acid or inorganic is formic acid, acetic acid, maleic acid, citric acid, fumaric acid, p-toluenesulfonic acid, picric acid, malic acid, glycine, hydrochloric acid, sulfuric acid, phosphoric acid, oxalic acid or methanesulfonic acid.

* * * * *

UNITED STATES PATENT AND TRADEMARK OFFICE
CERTIFICATE OF CORRECTION

PATENT NO.        : 8,884,021 B2                                Page 1 of 1
APPLICATION NO.   : 13/982095
DATED             : November 11, 2014
INVENTOR(S)       : Tian et al.

It is certified that error appears in the above-identified patent and that said Letters Patent is hereby corrected as shown below:

On the Title Page

Item (73) Assignees: "Topharman Shanghai Co., Ltd., Shanghai (CN); Topharman Shandong, Co., Ltd, Shandong (CN)" should be corrected to read: -- Topharman Shanghai Co., Ltd., Shanghai (CN); Shanghai Institute of Materia Medica, Chinese Academy of Sciences, Shanghai (CN); Topharman Shandong, Co., Ltd., Shandong (CN) --.

Signed and Sealed this
Twenty-first Day of July, 2015

Michelle K. Lee
*Director of the United States Patent and Trademark Office*